(12) United States Patent
Valet et al.

(10) Patent No.: US 11,896,649 B2
(45) Date of Patent: *Feb. 13, 2024

(54) METHODS AND PHARMACEUTICAL COMPOSITIONS FOR THE TREATMENT OF POST-OPERATIVE COGNITIVE DYSFUNCTION

(71) Applicants: INSERM (INSTITUT NATIONAL DE LA SANTE ET DE LA RECHERCHE MEDICALE), Paris (FR); UNIVERSITE PAUL SABATIER TOULOUSE III, Toulouse (FR); CENTRE HOSPITALIER UNIVERSITAIRE DE TOULOUSE, Toulouse (FR)

(72) Inventors: Philippe Valet, Toulouse (FR); Cedric Dray, Toulouse (FR); Vincent Minville, Toulouse (FR); Bernard Frances, Toulouse (FR); Francois Labaste, Toulouse (FR); Claire Vinel, Toulouse (FR)

(73) Assignees: INSTITUT NATIONAL DE LA SANTE ET DE LA RECHERCHE MEDICALE, Paris (FR); UNIVERSITE PAUL SABATIER TOULOUSE III, Toulouse (FR); CENTRE HOSPITALIER UNIVERSITAIRE DE TOULOUSE, Toulouse (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/935,667

(22) Filed: Sep. 27, 2022

(65) Prior Publication Data
US 2023/0093887 A1    Mar. 30, 2023

Related U.S. Application Data

(62) Division of application No. 16/077,949, filed as application No. PCT/EP2017/053308 on Feb. 14, 2017, now Pat. No. 11,484,577.

(30) Foreign Application Priority Data

Feb. 15, 2016 (EP) .................................. 16305170

(51) Int. Cl.
*A61K 38/22* (2006.01)
*A61K 31/015* (2006.01)
(Continued)

(52) U.S. Cl.
CPC ............ *A61K 38/22* (2013.01); *A61K 31/015* (2013.01); *A61K 31/02* (2013.01); *A61K 31/08* (2013.01);
(Continued)

(58) Field of Classification Search
CPC ...... A61K 38/22; A61K 31/015; A61K 31/02; A61K 31/08; A61K 33/00; A61P 25/28; A61P 23/00
See application file for complete search history.

(56) References Cited

U.S. PATENT DOCUMENTS

| | | | |
|---|---|---|---|
| 2012/0214143 A1* | 8/2012 | Severson | G16H 50/30 434/236 |
| 2013/0084299 A1* | 4/2013 | Maze | A61P 29/00 424/145.1 |
| 2014/0348883 A1* | 11/2014 | Reynolds | A61K 31/205 424/725 |

OTHER PUBLICATIONS

Telegdy et al., "Involvement of neurotransmitters in the action of apelin-13 on passive avoidance learning in mice", Peptides, 39 (2013), 171-174. (Year: 2013).*

(Continued)

*Primary Examiner* — Jianfeng Song
(74) *Attorney, Agent, or Firm* — WC&F IP

(57) ABSTRACT

The present invention relates to methods and pharmaceutical compositions for the treatment of post-operative cognitive dysfunction. In particular, the present invention relates to a
(Continued)

method of treating post-operative cognitive dysfunction in a subject in need thereof comprising administering to the subject a therapeutically effective amount of an APJ receptor agonist.

13 Claims, 4 Drawing Sheets

(51) Int. Cl.
    *A61P 25/28*     (2006.01)
    *A61P 23/00*     (2006.01)
    *A61K 31/02*     (2006.01)
    *A61K 31/08*     (2006.01)
    *A61K 33/00*     (2006.01)

(52) U.S. Cl.
    CPC .............. *A61K 33/00* (2013.01); *A61P 23/00* (2018.01); *A61P 25/28* (2018.01)

(56) References Cited

OTHER PUBLICATIONS

Li et al., "Apelin-13 exerts antidepressant-like and recognition memory improving activities in stressed rates", European Neuropsychopharmacology, 26, 420-430, Jan. 28, 2016. (Year: 2016).*

* cited by examiner

METHODS AND PHARMACEUTICAL COMPOSITIONS FOR THE TREATMENT OF POST-OPERATIVE COGNITIVE DYSFUNCTION

FIELD OF THE INVENTION

The present invention relates to methods and pharmaceutical compositions for the treatment of post-operative cognitive dysfunction.

BACKGROUND OF THE INVENTION

Postoperative cognitive dysfunction (POCD) is characterized by a persistent decline of cognitive performance after surgery and is associated with increased mortality in elderly patients. Estimated prevalence in patients over the age of 60 is 15-25% with approximately 10% exhibiting symptoms 3 months after surgery. Risk factors for POCD include increasing age, preoperative cognitive dysfunction and perioperative infection. There is currently no adequate treatment. Consistent evidence is accumulating for the role of inflammatory processes arising due to surgical trauma and subsequent complications. The hippocampus seems especially vulnerable to the inflammation. Peripheral infection and aging interact to impair hippocampal memory consolidation and aged rodents are more vulnerable to cognitive decline after a peripheral immune challenge (Barrientos et al., 2006; 2009; 2012). Central inflammatory responses, specifically cytokine increases in the hippocampus following surgery, have been repeatedly reported in rat and mouse models of POCD (Cao et al., 2010; Cibelli et al., 2010; Fidalgo et al., 2011a, 2011b; Rosczyk et al., 2008; Terrando et al., 2010; Wan et al., 2007, 2010).

As already mentioned, a proinflammatory context occurs after surgery associated to central anesthesia. This mechanism could be in part responsible for POCD by increasing hippocampic inflammation and altering neuronal plasticity. In elderly individuals, pro-inflammatory background has been described via different pathways and could be at the origin of many age-associated pathologies such as neurodegenerative diseases. During surgery, the acute phase of inflammation is counteracted by protective systems in child and adult. Such a protective system is altered in elderly patients since the inflammatory phase has been shown to be long lasting. Altogether, these data indicate that anti-inflammatory strategies should be processed in aged patients in order to reduce the risk to develop POCD. However, these approaches are not generally advised in elderlies due to the lack of tolerance of this population for non-steroidal anti-inflammatory drugs (NSAID) at renal or intestine level. Thus, new strategies are essential to fight against POCD when associated to pro-inflammatory context.

Apelin is a peptide synthetized and secreted by various tissues and retrieved in different species as a 77 amino-acids precursor. After endopeptidase cleavages, apelin is found in the circulation as four major isoforms: apelin-36, apelin 17, apelin-13 and the pyroglutaminated apelin-13. Apelin-13 is described as the most stable isoform in biological fluids. Apelin binds APJ, a G-protein coupled receptor present in the same tissues that its endogenous ligand apelin. Apelin/APJ complex is involved in osteogenesis, inflammation and neuroprotection. For example, in vitro apelin treatment of MC3T3-E1 osteoblasts shows a dose-dependent increase of proliferation associated to a decrease of apoptosis. Apelin is also associated to inflammatory processes. Indeed, even if the mechanisms are not fully understood, apelin production is increased by pro-inflammatory cytokines such as TNFalpha and thus could counteract inflammatory processes. Another very interesting property of apelin is its neuroprotective effect. Indeed, apelin-13 and -36 promote the survival of cultured hippocampal neurons induced by N-methyl-d-aspartate mediated toxicity of quinic acid. Another set of experiment shows that in NT2.N neurons, apelin-13 and -17 increase the phosphorylation of Raf, AKT and ERK1/2, and inhibits apoptosis induced by HIV. In cultured hippocampal neurons, apelin is significantly neuroprotective against hydrogen peroxide-toxicity when associated with vEGF. In cortical neurons, apelin-13 inhibits ROS production, mitochondrial depolarization, cytochrome c release from mitochondria into cytosol, caspase-3 activation, and apoptosis induced by serum deprivation. Moreover, apelin-13 attenuates serum deprivation-induced increase of phosphorylated ERK1/2. Apelin-13 also decreases phosphorylation of AKT indicating a protection of cultured cortical neurons against NMDA neurotoxicity, which highlights that apelin peptides may be neuroprotective against cerebral ischemia-reperfusion damage. Taken together these results indicate that apelin not only inhibits apoptosis but also antagonizes excitotoxicity in neural cells.

SUMMARY OF THE INVENTION

The present invention relates to methods and pharmaceutical compositions for the treatment of post-operative cognitive dysfunction. In particular, the present invention is defined by the claims.

DETAILED DESCRIPTION OF THE INVENTION

The inventors hypothesized that apelin could potentially be secreted in response to surgery-mediated inflammation and protect against neuronal injuries associated to POCD. To validate this hypothesis we chronically treated young and aged mice by daily i.p. administration of apelin and determined the impact of the treatment on memory, pain and stress after tibial fracture surgery. Moreover, to better assess the role of apelin during tibial surgery-mediated POCD, we measured the consequences of apelin administration on proinflammatory profile modification (TNFalpha, IL6 . . . ) in tissues.

A first object of the present invention relates to a method of treating post-operative cognitive dysfunction in a subject in need thereof comprising administering to the subject a therapeutically effective amount of an APJ receptor agonist.

As used herein the term "postoperative cognitive dysfunction" or "POCD" has its general meaning in the art and refers to a cognitive impairment experienced after surgery. POCD is a cognitive disorder including deterioration in memory, attention, learning, and speed of information processing. POCD can manifest as short-term symptom, or last for extended periods of time. In some circumstances, POCD can cause a permanent alteration of cognitive functions. Indeed, POCD is commonly observed after anesthesia. Methods for diagnosing POCD in a subject are known in the art. For examples, valid assessment of the subject's preoperative and postoperative cognitive function can be performed to characterize POCD. Typical neuropsychological tests known to a skilled artisan include, but not limited to, tests of verbal comprehension, perceptual organization, executive function (abstraction, problem solving and cognitive flexibility), visual tracking, game performance, psychomotor performance, psychomotor speed, digital symbol substitution, processing speed, dot-connection, flicker-fusion, simple reaction time, choice reaction time and perceptive accuracy.

As used herein, the term "treatment" or "treat" refer to both prophylactic or preventive treatment as well as curative or disease modifying treatment, including treatment of subject at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

In particular, the APJ receptor agonist of the present invention is particularly suitable for protecting the subject from neuronal injuries associated to POCD.

In some embodiments the method of the invention is performed on a subject who is determined to be at risk for postoperative cognitive dysfunction. In some embodiments, the method of the invention is performed on a subject who is diagnosed with or indicated to have an impairment in cognition.

In some embodiments, the APJ receptor agonist of the present invention is administered perioperatively; that is prior to, during and/or after surgery, and after hospital discharge.

As used herein the term "surgery" refers to any manual or operative methods or manipulations for the treatment or prevention of disease, injury or deformity. Surgery includes methods or manipulations conducted while a subject is under anesthesia, including local or general anesthesia. Surgery can be performed by a doctor, surgeon or dentist, generally in a hospital or other health care facility. Subjects undergoing surgery can be hospitalized or ambulatory, e.g., out-subject surgery. For purposes of this invention surgery includes, but is not limited to: abdominal surgery (e.g. surgery of the abdominal viscera), bench surgery (e.g. surgery performed on an organ that has been removed from the body, after which it can be reimplanted), cardiac (e.g. surgery of the heart), cerebral (e.g. surgery upon the brain), cineplastic (e.g. surgery to create a tunnel through a muscle adjacent to the stump of an amputated limb, to permit use of the muscle in operating a prosthesis), cosmetic (e.g. surgery to improve a subject's appearance by plastic restoration, correction or removal of blemishes), dentofacial (e.g. surgery involving defects of the face and structures of the mouth), neurological (e.g. surgery involving the peripheral or central nervous system), oral (e.g. surgery involving defects of the mouth, jaws and associated structures), orthopedic (e.g. surgery dealing with bones and bony structures such as hip replacement), pelvic (e.g. surgery involving the pelvis, predominately obstetrical and gynecological), plastic (e.g. surgery involving the restoration, reconstruction, correction or improvement in the shape and appearance of body structures that are defective, damaged or misshapened by injury, disease, or growth and development) or rectal (e.g. surgery of the rectum), urological (e.g. surgery related to the genitourinary system, predominately in males), vascular (e.g. surgery of the blood vessels), and surgery related to otolaryngology (e.g. surgery of the ears, nose, throat or related structures). The surgery can be conservative (e.g. surgery to preserve or remove with minimal risk, diseased or injured organs, tissues, or extremities) or radical (e.g. surgery designed to extirpate all areas of locally extensive disease and adjacent zones of lymphatic drainage).

In some embodiments, the APJ receptor agonist of the present invention is administered concomitantly or sequentially with an anesthetic to the subject. In some embodiments, the APJ receptor agonist and the anesthetic are administered, in either order, within a specific time of each other e.g. within 6 hours of each other, within 5 hours of each other, within 4 hours of each other, within 3 hours of each other, within 2 hours of each other, within 1 hour of each other, within 30 minutes of each other, within 20 minutes of each other, within 10 minutes of each other, within 5 minutes of each other, within 1 minute of each other or substantially simultaneously or concurrently. In some embodiments, the APJ receptor agonist of the present invention is administered to the subject prior to the anesthetic, e.g., about 6 hours, about 5 hours, about 4 hours, about 3 hours, about 2 hours, about 1 hour, about 30 minutes, about 20 minutes, about 10 minutes, about 5 minutes, or about 1 minute prior to administration of the anesthetic. In some embodiments, APJ receptor agonist of the present invention and the anesthetic can be administered concurrently.

As used herein, the term "anesthetic" has its general meaning in the art and refers to a drug that causes anesthesia, e.g., which is generally administered to facilitate a surgery, to relieve non-surgical pain or to enable diagnosis of a disease or disorder. Non-limiting examples of inhalational anesthetics include ethers such as diethyl ether, methoxypropane, vinyl ether, halogenated ethers, e.g., desflurane, enflurane, halothane, isoflurane, methoxyflurane; haloalkanes, such as chloroform, halothane, trichloroethylene, cyclopropane, ethylene, nitrous oxide, sevoflurane, xenon, deuterated isoflurane (disclosed in U.S. Pat. Nos. 4,220,644 and 4,262,144), hexafluoro-t-butyl-difluoromethyl ether (disclosed in U.S. Pat. No. 3,949,005), deutered analogues of methoxyflurane (disclosed in U.S. Pat. No. 4,281,020), deutered sevoflurane (disclosed in U.S. Pat. Nos. 5,391,579 and 5,789,450), and other inhalational anesthetic disclosed in the U.S. Patents, such as U.S. Pat. Nos. 3,931,344, 3,932,669, 3,981,927, 3,980,714, 4,346,246, 3,932,529, 3,932,667, 3,954,893, 3,987,100, 3,987,203, 3,995,062, the content of all which is incorporated herein by reference in its entirety. Any of the inhalational anesthetics can be used alone or in combination with other medications to maintain anesthesia. For example, nitrous oxide can be used in combination with other inhalational anesthetics.

As used herein the term "APJ receptor" has its general meaning in the art and refers to the receptor for apelin originally identified by O'Dowd et al. (O'Dowd et al, 1993, Gene 136: 355360). APJ is a 380 residue, 7 transmembrane domain, Gi coupled receptor whose gene is localized on the long arm of chromosome 11 in humans (NCBI Reference Sequence: NP-005152.1, and encoded by NCBI Reference Sequence: NM-005161). Although orphan for many years, the endogenous ligand has been isolated and named apelin (Tatemoto et al., Biochem Biophys Res Commun 251, 471-6 (1998)).

As used herein, the term "apelin" has its general meaning in the art and indicates a 77 residue preprotein (NCBI Reference Sequence: NP-0059109.3, and encoded by NCBI Reference Sequence: NM-017413.3), which gets processed into biologically active forms of apelin peptides, such as apelin-36, apelin-17, apelin-16, apelin-13, apelin-12. The full length mature peptide, referred to as "apelin-36," comprises 36 amino acids, but the most potent isoform is the pyroglutamated form of a 13mer of apelin (apelin-13), referred to as "Pyr-1-apelin-13 or Pyr1-apelin-13" Different apelin forms are described, for instance, in U.S. Pat. No. 6,492,324B1.

As used herein the term "APJ receptor agonist" refers to any compound, natural or not, capable of promoting the APJ receptor function. Examples of the APJ receptor agonists of the present invention include but are not limited to polypeptides, antibodies, aptamers and small organic molecules. Agonistic activities of a test compound toward APJ receptor may be determined by any well known method in the art. For example, since the agonist of the present invention can promote the function of the APJ receptor, the agonist can be screened using the natural agonist of APJ receptor (i.e. apelin) and its receptor. Typically, the agonist of the present invention can be obtained using the method screening the substance promoting the function of the APJ receptor, which comprises comparing (i) the case where apelin is brought in contact with the APJ receptor and (ii) the case where a test compound is brought in contact with the APJ receptor. In the screening method of the present invention, for example, (a) the binding amounts of apelin to the APJ receptor are measured (i) when apelin is brought in contact with the APJ receptor and (ii) apelin and a test compound are brought in contact with the APJ receptor; and comparing the results; or, (b) cell stimulating activities (e.g., the activities that promote arachidonic acid release, acetylcholine release, intracellular Ca2+ release, intracellular cAMP production, intracellular cGMP production, inositol phosphate production, changes in cell membrane potential, phosphorylation of intracellular proteins, activation of c-fos, pH changes, etc.) mediated by the APJ receptor are measured (i) when apelin is brought in contact with the APJ receptor and (ii) a test compound is brought in contact with the APJ receptor; and comparing the results. Typically, the test compounds that provide a higher promotion or at least the same promotion of APJ receptor than apelin are then selected as APJ receptor agonists. Specific examples of the screening method of the present invention include: (1) a method of screening the substance promoting the function of the APJ receptor, which comprises measuring the binding amounts of labeled apelin to the APJ receptor when the labeled apelin is brought in contact with the APJ receptor and when the labeled apelin and a test compound are brought in contact with the APJ receptor; and comparing the amounts; (2) a method of screening the substance promoting the function of the APJ receptor, which comprises measuring the binding amounts of labeled apelin to a cell containing the APJ receptor or a membrane fraction of the cell, when the labeled apelin is brought in contact with the cell or membrane fraction and when the labeled apelin and a test compound are brought in contact with the cell or membrane fraction, and comparing the binding amounts; and, (3) a method of screening the substance promoting the function of the APJ receptor, which comprises measuring the binding amounts of labeled apelin to the APJ receptor expressed on a cell membrane by culturing a transformant having a DNA encoding the APJ receptor, when the labeled apelin is brought in contact with the APJ receptor and when the labeled apelin and a test compound are brought in contact with the APJ receptor, and comparing the binding amounts. In those examples, the test compounds that provide a higher binding or at least the same binding as apelin are then selected as APJ receptor agonists. Specifically, a method for determining whether a compound is an APJ receptor agonist is described in Iturrioz X. et al. (Iturrioz X, Alvear-Perez R, De Mota N, Franchet C, Guillier F, Leroux V, Dabire H, Le Jouan M, Chabane H, Gerbier R, Bonnet D, Berdeaux A, Maigret B, Galzi J L, Hibert M, Llorens-Cortes C. Identification and pharmacological properties of E339-3D6, the first nonpeptidic apelin receptor agonist. FASEB J. 2010 May; 24(5):1506-17. Epub 2009 Dec. 29). The US Patent Application Publication No. US 2005/0112701 also described test system for the identification of a ligand for angiotension receptor like-1 (APJ receptor) comprising an APJ receptor. Another method is also described in the U.S. Patent Publication U.S. Pat. No. 6,492,324.

In some embodiments, the APJ receptor agonist is a small organic molecule. The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da. Examples of small organic molecules that are APJ receptor agonists include those described in the European Patent Application Publication No. EP19030052 and in Iturrioz X. et al. (Iturrioz X, Alvear-Perez R, De Mota N, Franchet C, Guillier F, Leroux V, Dabire H, Le Jouan M, Chabane H, Gerbier R, Bonnet D, Berdeaux A, Maigret B, Galzi J L, Hibert M, Llorens-Cortes C. Identification and pharmacological properties of E339-3D6, the first nonpeptidic apelin receptor agonist. FASEB J. 2010 May; 24(5):1506-17. Epub 2009 Dec. 29). Typically, a small organic molecule that is an APJ receptor agonist has the general formula (I):

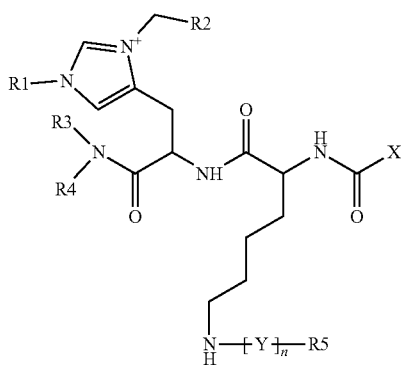

(I)

wherein:

R1 is an aryl, alkylaryl, heteroaryl or alkylheteroaryl group

R2 is a hydrogen atom or an aryl group

R3 and R4 represent a hydrogen atom or a heterocycloalkyl group providing that R3 and R4 cannot represent simultaneously a hydrogen and that R3 and R4 can both be part of a heterocycloalkyl group R5 represents a group selected from the group consisting of: boc, fmoc, texas red, patent blue V, lissamine, and rhodamine 101 n is an integer from 0 to 1

Y represents —CO—(NH)n'-A-NH— group with:

n' is an integer from 0 to 1

A is a group selected from the group consisting of:

—(CH2)n"—

—[(CH2)2—O]n'"—(CH2)2—

—(CH2)m—NH—CO—(CH2)m'—NH—CO—(CH2)m"—

—(CH2)m—CO—NH—(CH2)m'—

—(CH2)m—CO—NH—(CH2)m'—CO—NH—(CH2)m"— with n" representing an integer from 1 to 20 with n' representing an integer from 1 to 10 with m, m' and m" representing independently from the other an integer from 1 to 15

X represents a group chosen in the following list:

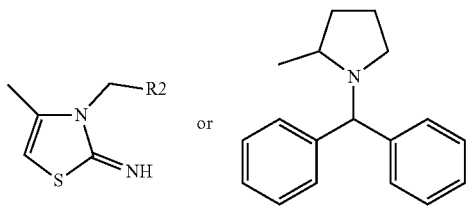

In some embodiments, the APJ receptor agonist consists in an antibody (the term including "antibody portion"). As used herein, "antibody" includes both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or non human antibody. A non human antibody may be humanized by recombinant methods to reduce its immunogenicity in man. Antibodies are prepared according to conventional methodology. Monoclonal antibodies may be generated using the method of Kohler and Milstein (Nature, 256:495, 1975). In some embodiments, antibody is a humanized antibody. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may used in designing the humanized antibodies. In some embodiments, the antibody is a human antibody. Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference. In some embodiments, the antibody is a single domain antibody. The term "single domain antibody" (sdAb) or "VHH" refers to the single heavy chain variable domain of antibodies of the type that can be found in Camelid mammals which are naturally devoid of light chains. Such VHH are also called "nanobody®". According to the invention, sdAb can particularly be llama sdAb.

In some embodiments, the APJ receptor agonist is an aptamer. Aptamers are a class of molecule that represents an alternative to antibodies in term of molecular recognition. Aptamers are oligonucleotide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA. In this library, each member is a linear oligomer, eventually chemically modified, of a unique sequence.

In some embodiments, the APJ receptor agonist consists in a polypeptide. In some embodiments, the polypeptide is an apelin polypeptide. The sequences of apelin polypeptides and nucleic acids for encoding such proteins are well known to those of skill in the art. According to the invention the term "apelin" polypeptide refers to any polypeptide that comprises the apelin-13 C-terminal fragment. Accordingly, the term encompasses apelin itself or fragments thereof comprising the apelin-17 or apelin-36 fragments. Other polypeptides that can be used as APJ receptor agonists include those described in U.S. Pat. Nos. 6,492,324, 7,635, 751, US2010221255, US2008182779, WO2013111110, WO2014081702, WO2014099984, WO201501316, WO2015013168 and WO2015013169.

In some embodiments, the polypeptide has the following formula:

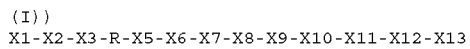

wherein:

X1 is the N-terminus of the polypeptide and is either absent or pE;

X2 is R or r;
X3 is P or 4-PhP;
X5 is L, Cha, D-L, F, Y, Y(Bzl), 3,4-Cl2-F or Nal;
X6 is a D-amino acid, S or A;
X7 is a D-amino acid, L, H or Aib; and at least one of X6 and X7 is D-amino acid or
Aib;
X8 is K, k, Q or E;
X9 is G or D;
X10 is P or pipecolic acid;
X11 is D-Nle, Nle, for D-Nva;
X12 is absent, P or a D-amino acid;
X13 is the C-terminus and is absent, F or a D-amino acid; and at least one of X11, X12 and X13 is a D-amino acid;
wherein:
Nle is L-norleucine;
D-Nle is D-norleucine;
Nal is L-naphthyl)alanine;
D-Nva is D-norvaline;
Aib is α-aminoisobutyric acid;
Cha is (S)-β-cyclohexylalanine;
D-Tic is D-1,2,3,4-tetrahydroisoquinoline-3-carboxylic acid;
pE is L-pyroglutamic acid;
3,4-Cl2-F is (S)-3,4-dichlorophenylalanine;
Y is L-tyrosine; and
Y(Bzl) is L-benzyl-tyrosine;
or an amide, an ester or a salt of the polypeptide.

In some embodiments, the polypeptide has the following formula:

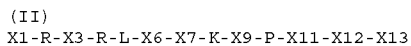

(II)
X1-R-X3-R-L-X6-X7-K-X9-P-X11-X12-X13 wherein
X1 is the N-terminus of the polypeptide and is absent or is selected from Q, A and pE;
X3 is P or X3 is selected from C, c, hC and D-hC; wherein the side chain of C, c, hC
or D-hC forms a disulfide bond with the side chain of X6;
X6 is selected from C, c, hC and D-hC, wherein the side chain of C, c, hC or D-hC
forms a disulfide bond with the side chain of C, c, hC or D-hC of either X3, X9 and X13;
X7 is H or Aib;
X9 is G or X9 is selected from C, c, hC and D-hC, wherein the side chain of C, c, hC
or D-hC forms a disulfide bond with the side chain of X6;
X11 is D-Nle, Nle, M or f;
X12 is absent or is P, for a;
X13 is absent, F, f, a, y or Nal or X13 is selected from C, c, hC and D-hC, wherein the side chain of C, c, hC or D-hC forms a disulfide bond with the side chain of X6;
and wherein only one of X3, X9 and X13 is selected from C, c, hC and D-hC;
Nle is L-norleucine;
D-Nle is D-norleucine;
D-hC is D-homocysteine
hC is L-homocysteine;
Nal is L-naphathaline;
Aib is 2-aminoisobutyric acid;
pE is L-pyroglutamic acid;
or an amide, an ester or a salt of the polypeptide; or a polypeptide substantially equivalent thereto.

According to the invention, the polypeptides are produced by any conventional automated peptide synthesis methods or by recombinant expression. General principles for designing and making proteins are well known to those of skill in the art.

In some embodiments, it is contemplated that the apelin polypeptide is modified in order to improve the therapeutic efficacy. Such modification(s) of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. For instance, polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule.

According to the invention, the APJ receptor agonist of the present invention is administered to the subject in a therapeutically effective amount. By a "therapeutically effective amount" is meant a sufficient amount of the active ingredient for treating the disease at reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination with the active ingredients; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Typically the APJ receptor agonist of the present invention is combined with pharmaceutically acceptable excipients, and optionally sustained-release matrices, such as biodegradable polymers, to form pharmaceutical compositions. The term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. In the pharmaceutical compositions of the present invention, the active ingredients of the invention can be administered in a unit administration form, as a mixture with conventional pharmaceutical supports. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

The invention will be further illustrated by the following figures and examples. However, these examples and figures should not be interpreted in any way as limiting the scope of the present invention.

FIGURES

Figure 4:
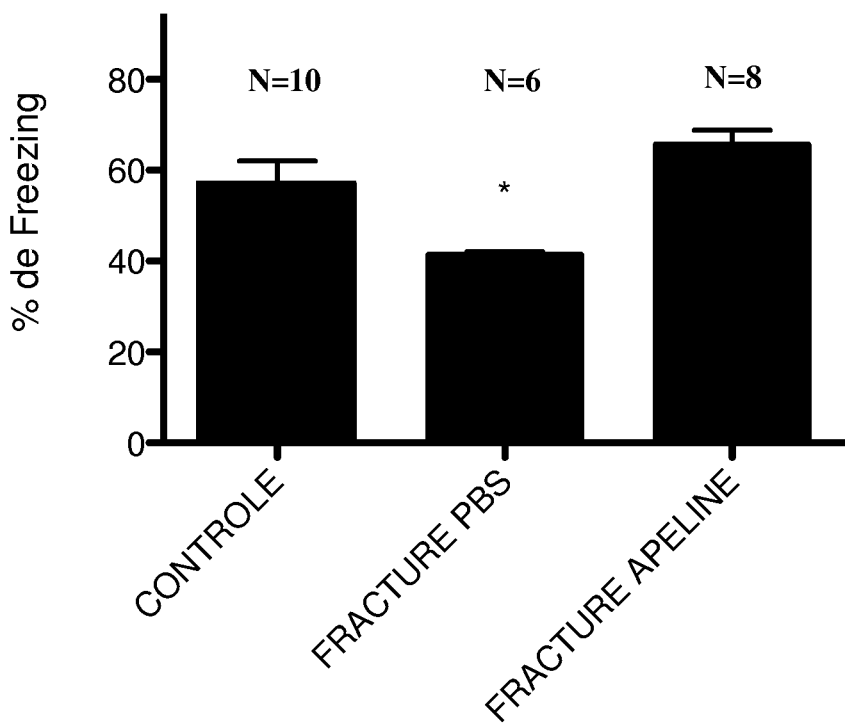

FIG. 4: Percentage of freezing in aged mice. Twenty month old male C57B16/j mice were fractured with (fracture apelin) or without (fracture PBS) an i.p treatment of apelin (0.5 nmol/kg) before and during 3 days after the fracture. After 3 days, animal hippocampal memory was tested by fear conditioning test. N=6 to 10, *p<0.05 compared to control.

Figure 5:
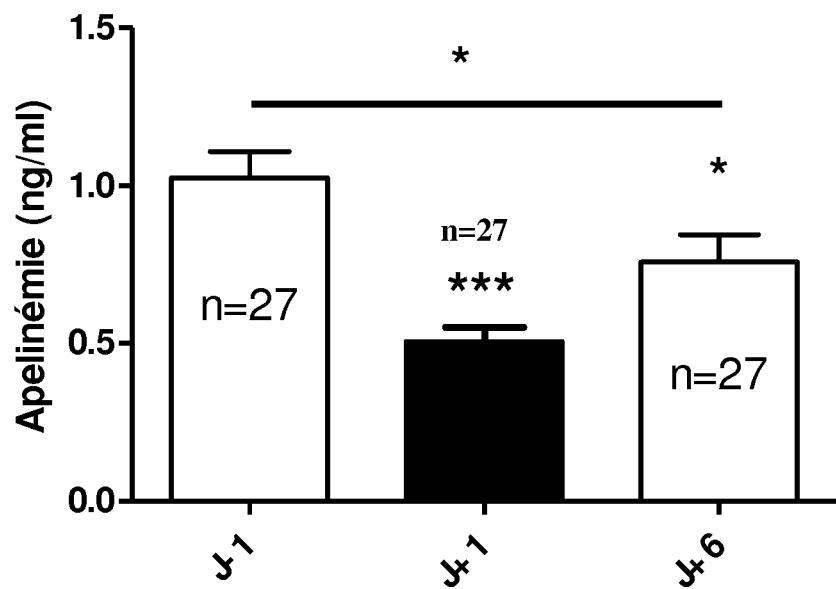

FIG. 5: Plasma apelin variation before and after a programmed hip replacement surgery. Blood was collected in patients 24 h before the surgery (J-1) or 24 h or 6 days later (J+1 and J+6). Plasma apelin was measured by a commercial ELISA test. In this study, patent are 60 years old and over.

EXAMPLE 1

Material & Methods

Surgery

All mice were anaesthetized with 2-3% sevoflurane. Adequate anesthesia was ascertained by an absent pedal withdrawal reflex after hard pinching of the toe. Closed tibial fracture was performed as previously described (Minville et al 2008). Briefly, after antiseptic preparation of the right paw with povidone-iodine, a unilateral closed fracture was produced in the right tibia using a specially designed fracture apparatus (blunt guillotine). For the intramedullary pinning using a sterile technique, a hole was made above the tibial tuberosity per-cutaneously using a 27 G needle (BD Microlance—27G ¾L 19 mm). Then, the needle was directed straight into the medullary canal. By rotating the needle, the canal was reamed to 5 mm up to the ankle joint. The end of the needle was cut as short as possible so that the skin could roll over and covers it. No suture was performed. The mouse was then placed with the leg on the anvil in order to line up the blunt guillotine with the proximal third of the tibia. A 300 g weight was decreased from a height of 9 to 10 cm, fracturing the tibia shaft. No movement response to injury occurred under these conditions.

Administration of Drugs

Apelin administration (ip, 0.5 umol/kg, Bachem) has been performed 1 hour before fracture and daily during the 15 consecutive days. Same volume of PBS has been injected in control mice.

Behavioral Tests

Mechanical Nociception

The animals were placed in cages equipped with a raised wire floor for the application of Von Frey filaments on the injured hind paw. A 15-min habituation period was observed. Von Frey filaments of increasing size were then applied to the plantar arch of the injured foot, to observe a characteristic pain response (paw withdrawal, triple flexion, licking of the paw, an association of these different responses). Each filament was applied to bend slightly for a 6-second period starting with the 0.6 g, and increasing until the positive response. The test was repeated 3 times, allowing a 5-min resting period between each test. The value of the lowest filament applied causing a positive response was considered as the threshold of mechanical nociception. The test was repeated at day 1, 5 and 15 after fracture.

Thermal Nociception

Thermal nociception was evaluated using the Hargreaves method. The animals were placed in individual cages equipped with a transparent window to allow the application of the light beam stimulus (4×6 mm with the light intensity that was previously set at 40% intensity maximum, so that it produces a heat of 52° C.). The light beam was applied at the hind paw. A 15-min habituation period was observed. The latency (in seconds) between the start of the application of the beam and a pain response was then measured. To avoid tissue damage, thermal stimulation did not exceed 20 s. The test was repeated 3 times, respecting a 5-min resting period. The shortest latency recorded was regarded as the threshold for thermal nociception. The test was repeated at day 1, 5 and 15 after fracture.

Fear Conditioning

To test the long-term memory and learning abilities, a fitness test to fear (Fear Conditioning Test) was used.

During the learning session, this test combines a painful and anxiety-producing event (2 short electrical discharges 0.3 mA 2 s on the legs) in an environmental context (floor cage with metal grills, washed several times a day with an alcoholic solution), visual (compound walls of black and white stripes, and white light patterns on the walls of the room) and sound (each discharge is preceded by a 80 dB sound 20 seconds). The learning phase lasted 4 minutes 25 seconds.

In the context of test sessions, conducted in the 3rd postoperative day, the animal was reintroduced in the same cage for 4 minutes. The context was the same but without sound stimulation or pain stimulus. If the animal was able to memorize the fact that this context is associated with a painful event, he engaged in conduct of fear, freezing, defined as total immobility except for respiratory movements. Operator who ignored the treatment received by each animal evaluated the freezing time of each animal. The blind was lifted at the end of all manipulations. This rugged test requires a proper functioning of the hippocampus, but also the amygdala and cortex. This test has been used to diagnose post-operative cognitive impairment in animal models in several publications. The test was performed at day 3 after fracture.

Tissues Collection 72 hours after fracture, mice were euthanatized by rapid carotid section and decapitation. Hippocampus and hematoma were rapidly collected and snap frozen. Blood was collected during carotid section, centrifuged and plasma was snap frozen.

mRNA Expression of Proinflammatory Cytokines

IL-6 and TNFa mRNA levels were measured by RT-PCR technique (see Dray et al. Cell metabolism 2008).

Results

Figure 1:
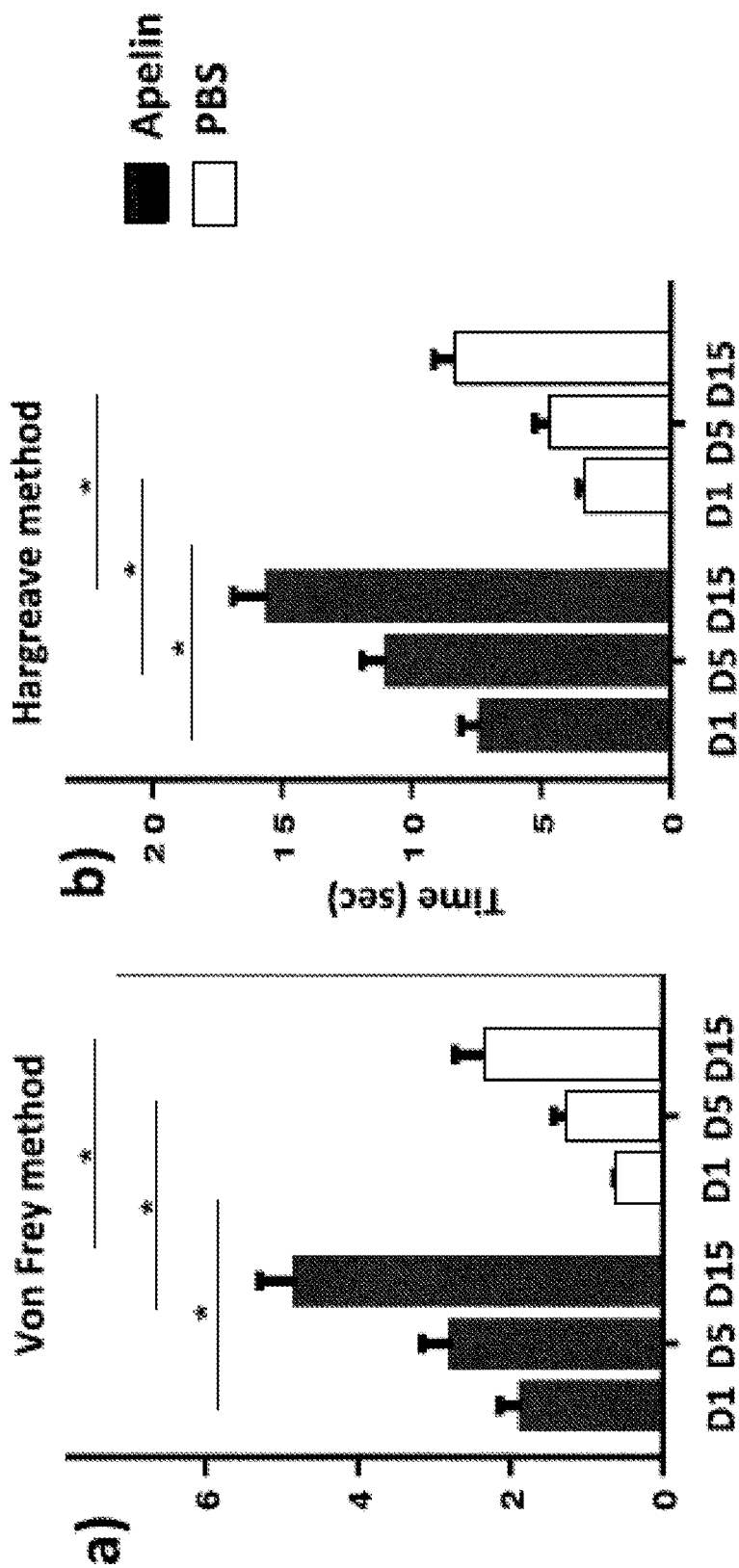
FIG. 1 shows that pain and nociception measured by Von Frey or Hargreave's techniques are significantly decreased by apelin treatment as respectively shown in FIGS. 1a and 1b.

Pain is reduced by apelin treatment
Pain and nociception measured by Von Frey or Hargreave's techniques are significantly decreased by apelin treatment as respectively shown in FIGS. 1a and 1b.

Daily treatment with apelin increases the freezing carried out in mice.

Figure 2:
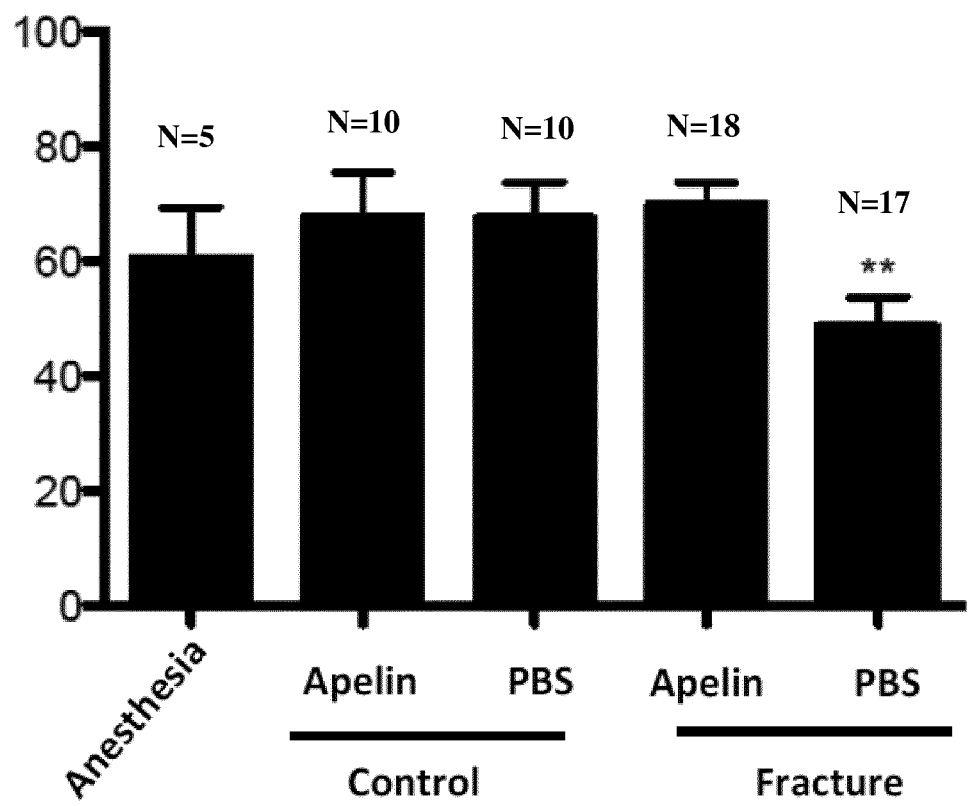
FIG. 2 shows that Daily treatment with apelin increases the freezing carried out in mice.

Postoperative, the operated mice developed cognitive impairment (FIG. 2). Indeed, when tested in the context made to the third days post-surgery, the operated animals showed freezing rate statistically lower than those of non-operated animals. These manipulations have validated once again the animal model developed by our team. The operated mice that received a daily injection of apelin had a freezing rate increased compared to mice receiving operated saline injections (FIG. 2). The non-operated mice treated by apelin did not display change in their rate of freezing.

Inflammatory Status

Figure 3:
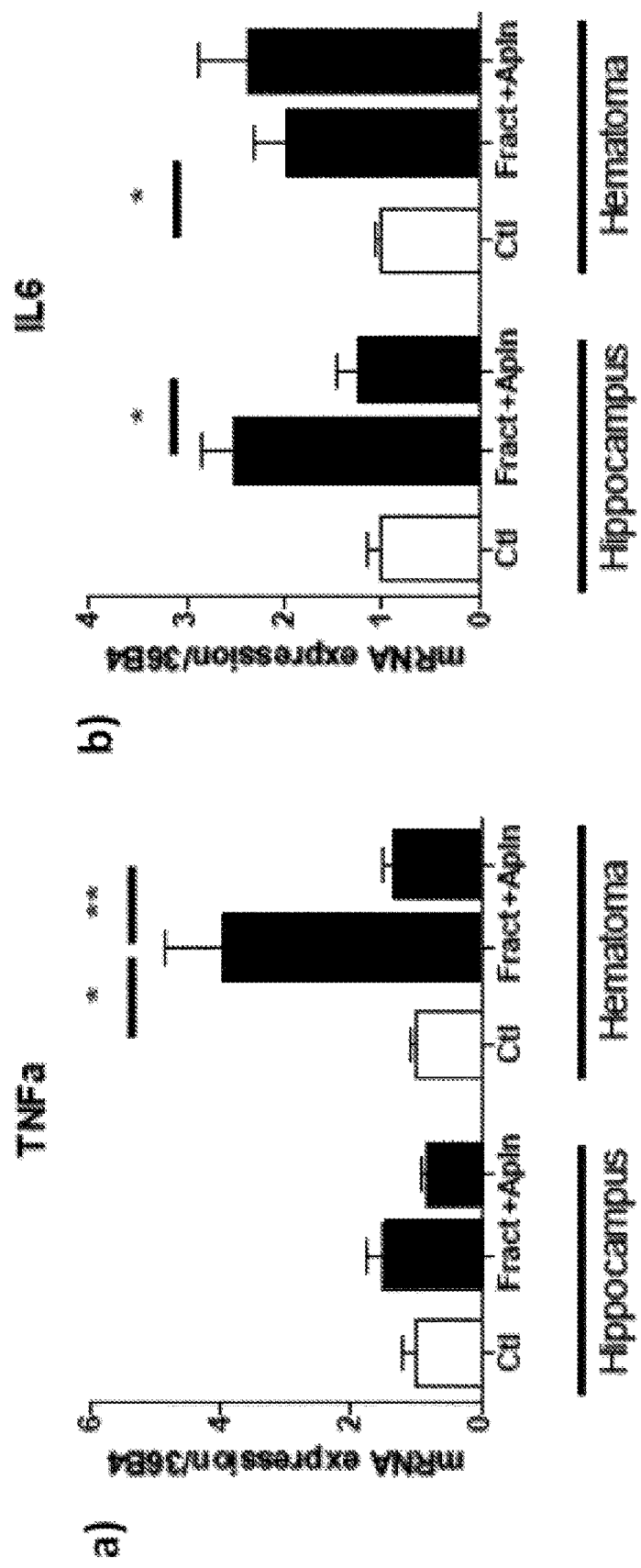
FIG. 3 shows that apelin treatment decreased hematoma TNFa mRNa and hyppocampus IL-6 mRNA expression in fractured mice.

Apelin treatment decreased hematoma TNFa mRNa and hyppocampus IL-6 mRNA expression in fractured mice. Fractured mice treated by apelin exhibited a strong decreased of the proinflammatory cytokine TNFa in the hematoma (FIG. 3a). Associated to this decrease, apelin treatment is able to avoid IL-6 increase in hippocampus of fractured mice (FIG. 3b).

EXAMPLE 2

Material & Methods

See Material & Methods of EXAMPLE 1

Results

FIG. 4 shows that in spite of their age (20 months old) animals treated with apelin are still sensitive to the peptide since they do not exhibit hippocampal memory failure after the fracture. In another hand, animals treated with PBS display a decrease of freezing compared to 3 months old animal.

EXAMPLE 3

Material & Methods

Patients are 60 years old and over with 56% of males. They do not display any significant pathologies (cancer, heart failure . . . ) associated to a potential treatment. These patients are programmed for surgery aiming to a hip replacement.

Results

FIG. 5 shows a plasma apelin variation in response to surgery with a decrease in apelin 24 h after surgery and a normalization of apelin amounts in blood after 6 days.

REFERENCES

Throughout this application, various references describe the state of the art to which this invention pertains. The disclosures of these references are hereby incorporated by reference into the present disclosure.

The invention claimed is:

1. A method of treating post-operative cognitive dysfunction in a subject in need thereof comprising administering to the subject at least one dose of a therapeutically effective amount of an APJ receptor agonist, wherein the APJ receptor agonist is apelin-13;
wherein the cognitive impairment is measured prior to and/or following the surgery by performing at least one neuropsychological test to test a function selected from the group consisting of verbal comprehension, perceptual organization, executive function, abstraction, problem solving, cognitive flexibility, visual tracking, game performance, psychomotor performance, psychomotor speed, digital symbol substitution, processing speed, dot-connection, flicker-fusion, simple reaction time, choice reaction time and perceptive accuracy;
wherein the at least one dose of the therapeutically effective amount of the APJ receptor agonist is administered within six hours prior to administration of an anesthetic and/or within six hours following administration of an anesthetic;
wherein the route of administration is selected from the group consisting of oral, implant, subcutaneous, transdermal, topical, intraperitoneal, intramuscular, intravenous, subdermal, transdermal, intranasal and rectal; and
wherein the therapeutically effective amount of the APJ receptor agonist is sufficient to reduce or ameliorate the cognitive impairment caused by surgery.

2. The method of claim 1, wherein the subject is determined to be at risk for post-operative cognitive dysfunction.

3. The method of claim 1, wherein the subject is diagnosed with or indicated to have impairment in cognition.

4. The method of claim 1, wherein the post-operative cognitive dysfunction is cognitive impairment experienced after surgery selected from the group consisting of abdominal surgery, bench surgery, cardiac surgery, cerebral surgery, cineplastic surgery, cosmetic surgery, dentofacial surgery, neurological surgery, oral surgery, orthopedic surgery, pelvic surgery, plastic surgery, rectal surgery, urological surgery, vascular surgery, and otolaryngology surgery.

5. The method of claim 1, wherein the APJ receptor agonist is administered concomitantly or sequentially with an anesthetic to the subject.

6. The method of claim 5, wherein anesthetic is selected from the group consisting of diethyl ether, methoxypropane, vinyl ether, halogenated ethers, haloalkanes, trichloroethylene, cyclopropane, ethylene, nitrous oxide, sevoflurane, xenon, deuterated isoflurane, hexafluoro-t-butyl-difluoromethyl ether, a deutered analogue of methoxyflurane, and deutered sevoflurane.

7. The method of claim 4, wherein
the abdominal surgery is surgery of the abdominal viscera;
the bench surgery is surgery performed on an organ that has been removed from the body;
the cineplastic surgery is surgery to create a tunnel through a muscle adjacent to a stump of an amputated limb to permit use of the muscle in operating a prosthesis;
the cosmetic surgery is surgery to improve the subject's appearance by plastic restoration, correction or removal of blemishes;
the dentofacial surgery is surgery to correct defects of the face and structures of the mouth;
the neurological surgery is surgery involving the peripheral or central nervous system;
the pelvic surgery is obstetrical and/or gynaecological surgery;
the oral surgery is surgery to correct defects of the mouth, jaws and associated structures;
the orthopedic surgery is hip replacement;
the plastic surgery is surgery involving restoration, reconstruction, correction or improvement in shape and appearance of body structures that are defective, damaged or misshapened by injury, disease, or growth and development;
the urological surgery is surgery of the male genitourinary system; and
the otolaryngology surgery is surgery of the ears, nose, throat or related structures.

8. The method of claim 6, wherein
the halogenated ether is desflurane, enflurane, halothane, isoflurane, or methoxyflurane; and
the haloalkane is chloroform or halothane.

9. A method of treating or inhibiting post-operative cognitive dysfunction in a subject in need thereof, comprising
administering to the subject at least one dose of a therapeutically effective amount of an APJ receptor agonist, wherein the APJ receptor agonist is apelin-13;
wherein the at least one dose of the therapeutically effective amount of the APJ receptor agonist is sufficient to reduce or ameliorate a cognitive impairment of memory, attention, learning and/or speed of information processing caused by an anesthetic administered for a surgery;
wherein the cognitive impairment is measured prior to and/or following the surgery by performing at least one neuropsychological test to test a function selected from the group consisting of verbal comprehension, perceptual organization, executive function, abstraction, problem solving, cognitive flexibility, visual tracking, game performance, psychomotor performance, psychomotor speed, digital symbol substitution, processing speed, dot-connection, flicker-fusion, simple reaction time, choice reaction time and perceptive accuracy,
wherein the at least one dose is administered within six hours prior to and/or within six hours following administration of the anesthetic; and
wherein the route of administration is selected from the group consisting of oral, implant, subcutaneous, transdermal, topical, intraperitoneal, intramuscular, intravenous, subdermal, transdermal, intranasal and rectal.

10. The method of claim 1, further comprising a step of repeating the administering step daily for as many as 15 days.

11. The method of claim 1, further comprising a step of repeating the administering step daily for at least 3 days.

12. The method of claim 9, further comprising a step of repeating the administering step daily for as many as 15 days.

13. The method of claim 9, further comprising a step of repeating the administering step daily for at least 3 days.

* * * * *